US007122341B1

(12) United States Patent
Liao

(10) Patent No.: US 7,122,341 B1
(45) Date of Patent: ＊Oct. 17, 2006

(54) ENGINEERING OF METABOLIC CONTROL

(75) Inventor: James C. Liao, Los Angeles, CA (US)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/048,186

(22) PCT Filed: Jul. 27, 2000

(86) PCT No.: PCT/US00/20519

§ 371 (c)(1),
(2), (4) Date: Jun. 19, 2002

(87) PCT Pub. No.: WO01/07567

PCT Pub. Date: Feb. 1, 2001

Related U.S. Application Data

(60) Provisional application No. 60/145,801, filed on Jul. 27, 1999.

(51) Int. Cl.
*C12N 1/21* (2006.01)
*C12N 15/11* (2006.01)
*C12P 23/00* (2006.01)
*C12Q 1/68* (2006.01)

(52) U.S. Cl. ................. 435/67; 435/252.33; 435/6; 435/71.1; 435/233; 536/23.2; 536/24.1

(58) Field of Classification Search ............. 435/252.3, 435/6, 252.33, 67, 71.1, 283, 252.31, 252.2; 536/23.2, 24.1
See application file for complete search history.

(56) References Cited

U.S. PATENT DOCUMENTS

| | | | |
|---|---|---|---|
| 5,429,939 A | 7/1995 | Misawa et al. ............... | 435/67 |
| 5,530,189 A | 6/1996 | Ausich et al. ............... | 800/205 |
| 5,744,341 A | 4/1998 | Cunningham, Jr. et al. . | 435/189 |
| 5,830,692 A * | 11/1998 | Bock et al. ................ | 435/69.1 |
| 5,906,925 A | 5/1999 | Liao ........................... | 435/72 |
| 2002/0045220 A1 * | 4/2002 | Khosla et al. ............... | 435/76 |

FOREIGN PATENT DOCUMENTS

WO          96/08567      *   3/1996

OTHER PUBLICATIONS

S. Kajiwara et al. "Expression of an Exogenous Isopentenyl Diphosphate Isomerase Gene Enhances Isoprenoid Biosynthesis i *Escherichia coli*", Biochemical J. 324: 421-426. (1997).*

Campos-Garcia et al., "The *pseudomonas aeruginosa rhlG* gene encodes an NADPH-dependent β-Ketoacyl which is specifically involved in rhamnolipid synthesis", *Journal of Bacteriology* 180 (17):4442-4451 (1998).

Farmer et al., "Reprogramming the regulatory circuits of *Escherichia coli*", Abstract 083., American Chemical Society National Meeting, Boston, MA Aug. 23-27 (1998).

Farmer et al., "Reprogramming the regulatory circuits of *Escherichia coli*", Abstract 094., American Chemical Society National Meeting, Anaheim, CA Mar. 21-25 (1999).

Feng et al., "Role of phosphorylated metabolic intermediates in the regulation of glutamine synthetase synthesis in *Escherichia coli*", *Journal of Bacteriology* 174(19):6061-6070 (1992).

Haldimann et al., "Transcriptional regulation of the *Enterococcus faecium* BM4147 vancomycin resistance gene cluster by the VanS-VanR two-component regulatory system in *Escherichia coli* K-12", *Journal of Bacteriology* 179(18):5903-5913 (1997).

McCleary et al., "Acetyl phosphate a global signal in *Escherichia coli?*", *Journal of Bacteriology* 175(10):2793-2798 (1993).

McCleary et al., "Acetyl phophate and the activation of two-component response regulators", *Journal of Biological Chemistry* 269(50):31567-31572 (1994).

Misawa et al., "Elucidation of the *Erwinia uredovora* carotenoid biosynthetic pathway by functional analysis of gene products expressed in *Escherichia coli*", *Journal of Bacteriology* 172(12):6704-6712 (1990).

Ruther et al., "Production of zeaxanthin in *Escherichia coli* transformed with different carotenogenic plasmids", *Appl Microbiol Biotechnol* 48:162-167 (1997).

Schroeckh et al., "Formation of recombinant proteins in *Escherichia coli* under control of a nitrogen regulated promoter at low and high cell densities", *Journal of Biotechnology* 49:45-58 (1996).

Scroeckh et al., "The use of elements of the *E. coli* Ntr-system for the design of an optimized recombinant expression system for high cell density cultivations". *Journal of Biotechnology* 75:241-250 (1999).

Shin et al., "Modulation of flagellar expression in *Escherichia coli* by acetyl phosphate and the osmoregulator OmpR", *Journal of Bacteriology* 177(16):4696-4702 (1995).

Sprenger et al., "Identification of a thiamin-dependent synthase in *Escherichia coli* required for the formation of the 1-deoxy-D-xylulose 5-phosphate precursor to isoprenoids, thiamin, and pyridoxol", *Proc. Natl. Acad. Sci USA* 94:12857-12862 (1997).

Wang et al., "Engineered Isoprenoid pathway enhances Astaxanthin production in *Escherichia coli*", *Biotechnology and Bioengineering* 62(2):235-241 (1999).

Alex and Simon, "Protein histidine kinases and signal transduction in prokaryotes and eukaryotes", *Trends in Genetics* 10(4):133-138 (1994).

Aristidou et al., "Metabolic engineering of *Escherichia coli* to enhance recombinant protein production through acetate reduction", *Biotechnol. Prog.* 11:475-478 (1995).

(Continued)

*Primary Examiner*—Rebecca Prouty
(74) *Attorney, Agent, or Firm*—Fish & Richardson P.C.

(57) ABSTRACT

The invention features a method of producing heterologous molecules in cells under the regulatory control of a metabolite and metabolic flux. The method can enhance the synthesis of heterologous polypeptides and metabolites.

14 Claims, No Drawings

OTHER PUBLICATIONS

Bauer et al., "Improved expression of human interleukin-2 in high-cell-density fermentor cultures of *Escherichia coli* K-12 by a phosphotransacetylase mutant", *Appl Environ Microbiol.* 56(5):1296-1302 (1990).

DeWitt et al., This Month in *Nature Biotechnology, Nature Biotechnology* 18:480 (2000).

Diez-Gonzalez and Russell, "The ability of *Escherichia coli* O157:H7 to decrease its intracellular pH and resist the toxicity of acetic acid", *Microbiology* 143:1175-1180 (1997).

Farmer and Liao, "Improving lycopene production in *Escherichia coli* by engineering metabolic control," *Nature Biotechnol.* 18:533-537 (2000).

Hakenbeck and Stock, "Analysis of Two-Component Signal Transduction Systems Involved in Transcriptional Regulation", *Methods in Enzymology* 273:281-301 (1996).

Parkinson and Kofoid, "Communication Modules in Baterial Signaling Proteins", *Annu. Rev. Genet.* 26:71-112 (1992).

Sevenich et al., "DNA binding and oligomerization of NtrC studied by fluorescence anisotropy and fluorescence correlation spectroscopy", *Nucleic Acid Res.* 26(6):1373-1381 (1998).

Reitzer et al., "Expression of *glnA* in *Escherichia coli* is regulated at tandem promoters", *Proc. Natl. Acad. Sci. USA* 82:1979-1983 (1985).

Wanner et al., "Involvement of Phosphotransacetylase, Acetate Kinase, and Acetyl Phosphate Synthesis in Control of the Phosphate Regulon in *Escherichia coli*", *J. Bacteriol.* 174(7):2124-2130 (1992).

Albrecht, M. et al., "Metabolic Engineering of the Terpenoid Biosynthetic Pathway of *Escherichia coli* for Production of the Carotenoids β-Carotene and Zeaxanthin", *Biotechnology Letters* vol. 21, pp. 791-795, XP009007288; 1999.

Matthews, P.D and Wurtzel E.T., "Metabolic Engineering of Carotenoid Accumulation in *Echerichia coli* by Modulation of the Isoprenoid Precursor pool with Expression of Deoxyxylulose Phosphate Synthase", *Applied Microbiology Biotechnology*, vol. 53, pp. 396-400, XP-000941210; 2000.

Misawa N. and Shimada H., "Metabolic Engineering for the Production of Carotenoids in Non-Carotenogenic Bacteria and Yeasts", *Journal of Biotechnology*, vol. 59, pp. 169-181, 1998.

Patnaik R. and Liao, J.C., "Engineering of *Escherichia coli* Central Metabolism for Aromatic Metabolite Production with Near Theoretical Yield", *Applied and Environmental Microbiology*, vol. 60, No. 11, pp. 3903-3908, XP 000610868, 1994.

Patnaik, R. et al., "Pathway Engineering for Production of Aromatics in *Echerichia coli*: Confirmation of Stoichiometric Analysis by Independent Modulation of AroG, TktA, and Pps Activities", *Biotechnology and Bioingineering*, vol. 46, pp. 361-370, XP-000882934, 1995.

Sandmann, G. et al., "The Biotechnological Potential and Design of Novel Carotenoids by Gene Combination in *Echerichia coli*", *Trends in Biotechnology, Reviews*, vol. 17, pp. 233-237, 1999.

Schmidt-Dannert, C., "Engineering Novel Carotenoids in Microorganisms", *Current Opinion in Biotechnology*, vol. 11, pp. 255-261, XP000985860, 2000.

Shimada, H. et al., "Increased Carotenoid Production by the Food Yeast *Candida utilis* through Metabolic Engineering of Isoprenoid Pathway", *Applied and Environmental Microbiology*, vol. 64, No. 7, pp. 2676-2680, XP-002269481, 1998.

Communication dated Feb. 26, 2004 for EP 00 95 0804.5 (8 pages).

* cited by examiner

ENGINEERING OF METABOLIC CONTROL

This application claims the benefit of U.S. provisional application 60/145,801, filed Jul., 27, 1999.

GOVERNMENT RIGHTS

This invention was made with Government support under Grant DE-FG03-98ER20298 with the U.S. Department of Energy and Grant BES-9814097 with the National Science Foundation. The Government has certain rights in the invention.

BACKGROUND OF THE INVENTION

The use of recombinant DNA technology has allowed the engineering of host cells to produce desired compounds, such as polypeptides and secondary metabolites. The large scale production of polypeptides in engineered cells allows for the production of proteins with pharmaceutical uses and enzymes with industrial uses. Secondary metabolites are products derived from nature that have long been known for their biological and medicinal importance. Because of the structural complexity inherent in such molecules, traditional chemical synthesis often requires extensive effort and the use of expensive precursors and cofactors to prepare the compound. In recent years, the expression of heterologous proteins in cells has facilitated the engineering of heterologous biosynthetic pathways in microorganisms to produce metabolites from inexpensive starting materials. In this manner, a variety of compounds have been produced, including polyketides, β-lactam antibiotics, monoterpenes, steroids, and aromatics.

SUMMARY OF THE INVENTION

The invention is based, in part, on the discovery that production of heterologous polypeptides and metabolites can be enhanced by the regulated expression of the polypeptide (e.g., a biosynthetic enzyme) using a promoter which is regulated by the concentrations of a second metabolite, e.g. acetyl phosphate. The term "heterologous" refers to a polypeptide or metabolite which is introduced by artifice. A heterologous polypeptide or metabolite can be identical to endogenous entity that is naturally present. The term "metabolite" refers to a organic compound which is the product of one or more biochemical reactions. A metabolite may itself be a precursor for other reactions. A secondary metabolite is a metabolite derived from another.

Accordingly, in one aspect, the invention features a bacterial host cell containing a nucleic acid sequence comprising a promoter and a nucleic acid sequence encoding a heterologous polypeptide. Examples of bacterial host cells include *Escherichia coli, Bacillus subtilis, Salmonella typhimurium, Agrobacterium tumefaciens, Thermus thermophilus*, and *Rhizobium leguminosarum* cells. The nucleic acid sequence is operably linked to the promoter which is controlled by a response regulator protein. In other words, the nucleic acid sequence is linked to the promoter sequence in a manner which allows for expression of the nucleotide sequence in vitro and in vivo. "Promoter" refers to any DNA fragment which directs transcription of genetic material. The promoter is controlled by a response regulator protein, for example, ntrC, phoB, phoP, ompR, cheY, creB, or torR, of *E. coli* or its homologs from other bacterial species. Further, the response regulator protein can be another member of the cluster orthologous group (COG) COG0745 as defined by www.ncbi.nlm.nih.gov/COG/(Tatusov et al. *Nucleic Acids Res.* (2000); 28:33–36). In one implementation, the promoter is bound by *E. coli* ntrC. The term "ntrC" refers to both the *E. coli* ntrC protein (SWISSPROT: P06713) www.expasy.ch/ and its homologs in other bacteria as appropriate. As used herein, "bound" refers to a physical association with a equilibrium binding constant ($K_D$) of less than 100 nM, preferably less than 1 nM. An example of the promoter is the *E. coli* glnAp2 promoter, e.g. a region between positions about 93 and about 323 in the published DNA sequence, GenBank accession no. M10421(Reitzer & Magasanik (1985) Proc Nat Acad Sci USA 82:1979–1983). This region includes untranslated sequences from the glnA gene. Further, a translational fusion can be constructed between coding sequences for glnA and coding sequences for the heterologous polypeptide.

The host cell is genetically modified such that the promoter is regulated by acetyl phosphate in the absence of nitrogen starvation. For example, the host cell can genetically modified by deletion or mutation of a gene encoding a histidine protein kinase, e.g., a member of COG0642 as defined by (http://www.ncbi.nlm.nih.gov/COG/; Tatusov et al. supra.), e.g., glnL, phoR, phoQ, creC, or envZ. In another example, the histidine protein kinase has specificity for the response regulator protein which controls the promoter. The histidine protein kinase can be encoded by glnL, e.g., *E. coli* glnL (SWISSPROT P06712; www.expasy.ch/).

Whereas the host cell is genetically modified such that the promoter is regulated by acetyl phosphate in the absence of nitrogen starvation, for heterologous polypeptide or metabolite expression, the host cell can be propagated in any desired condition, e.g., in nitrogen starvation conditions, nitrogen poor conditions, or nitrogen rich conditions.

The heterologous polypeptide encoded by the nucleic acid sequence can be a biosynthetic enzyme required for production of a metabolite. It can be a mammalian protein, e.g., a secreted growth factor, a monoclonal antibody, or an extracellular matrix component. In yet another example, the heterologous polypeptide can be a desired antigen for use in a vaccine, e.g., a surface protein from a viral, bacterial, fungal, or protist pathogen.

Another aspect of the invention features a kit containing a nucleic acid sequence which includes a promoter controlled by a response regulator protein. The kit further optionally contains a bacterial host cell which is genetically modified such that the promoter is regulated by acetyl phosphate in the absence of nitrogen starvation. The kit can also provide instructions for their use. The nucleic acid sequence can contain a restriction enzyme polylinker located 3' of the promoter such that a sequence inserted into the polylinker is operably linked to the promoter which is controlled by a response regulator protein. In one implementation of the kit, the promoter is the *E. coli* glnAp$_2$, promoter and the bacterial host cell is an *E. coli* cell containing a mutation or deletion of the glnL gene.

Another aspect of the invention features a host cell containing a first expression cassette. The first expression cassette includes a promoter, such as any of those described above, and a nucleic acid sequence encoding an enzyme required for biosynthesis of a heterologous metabolite. As used herein, "enzyme" refers to a polypeptide having ability to catalyze a chemical reaction or multiple reactions. The nucleic acid sequence is operably linked to the promoter which is regulated by acetyl phosphate in the absence of nitrogen starvation. The host cell also contains additional nucleic acid sequences for expressing other enzymes required for biosynthesis of the metabolite. Such additional sequences may be endogenous sequences expressing endogenous enzymes, or introduced sequences expressing heterologous enzymes.

In one example, the heterologous metabolite is an isoprenoid, a polyhydroxyalkanoate, a polyketide, a β-lactam antibiotic, an aromatic, or a precursor, e.g., an upstream metabolite, or a derivative, e.g., a downstream metabolite, thereof. For instance, the isoprenoid can be a carotenoid, a sterol, a taxol, a diterpene, a gibberellin, and a quinone. Specific examples of isoprenoids include isopentyl diphosphate, dimethylallyl diphosphate, geranyl diphosphate, farnesyl diphosphate, geranylgeranyl diphosphate, and phytoene. Specific examples of carotenoids include β-carotene, ξ-carotene, astaxanthin, zeaxanthin, zeaxanthin-β-glucoside, phytofluene, neurosporene, lutein, and torulene. When the desired heterologous metabolite is an isoprenoid, the heterologous enzyme can be isopentenyl diphosphate isomerase, geranylgeranyl diphosphate synthase, or 1-deoxyxylulose 5-phosphate synthase. When the desired heterologous metabolite is an polyhydroxyalkanoate, the heterologous enzyme can be 3-ketoacyl reductase, or poly-3-hydroxyalkanoate polymerase.

The host cell can be a bacterial cell, e.g., an *E. coli* cell. The host cell is optionally genetically modified by deletion or mutation of a gene, e.g., a gene encoding a histidine protein kinase, as described above. In one specific example, the host cell further contains a second expression cassette containing a nucleic acid sequence encoding phosphoenolpyruvate synthase operably linked to a promoter regulated by acetyl phosphate concentration, e.g., glnAp$_2$.

Another aspect of invention features a method of producing heterologous isoprenoids in a host cell. The method includes overexpressing phosphoenolpyruvate synthase and expressing biosynthetic enzymes required for synthesis of the heterologous isoprenoid. In one implementation, a gene in the host cell encoding a pyruvate kinase or a phosphoenolpyruvate carboxylase is genetically deleted or enfeebled. In another implementation, a gene encoding phosphoenolpyruvate carboxykinase is overexpressed in the host cell. Still another aspect of the invention features a method of producing a lycopene in a host cell. The method includes expressing the following heterologous enzymes: 1-deoxy-D-xylulose 5-phosphate synthase, a geranylgeranyl diphosphate synthase, a phytoene synthase, and a phytoene saturase. In one implementation of this method, an isopentenyl diphosphate isomerase is overexpressed, e.g., using the glnAp2 promoter. In another implementation, a phosphoenolpyruvate synthase is overexpressed, e.g., using the glnAp2 promoter.

Another aspect of the invention features a nucleic acid sequence containing a promoter and a sequence encoding a biosynthetic enzyme required for the production of a first metabolite. The promoter is operably linked to the sequence, and is regulated by a second metabolite whose concentration is indicative of availability of a precursor for the biosynthesis of the first metabolite. In one example, the second metabolite is a waste product produced from a precursor for the biosynthesis of the first metabolite.

In one implementation, the first metabolite is a polyhydroxyalkanoate, e.g., polyhydroxybutyrate and the nucleic acid sequence encodes a biosynthetic enzyme, e.g., a 3-ketoacyl coenzyme A (coA) reductases, or a poly-3-hydroxyoctanoyl-CoA polymerase. In another case, the first metabolite is a polyketide, a β-lactam antibiotic, or an aromatic. In a yet another case, the first metabolite is an isoprenoid, e.g., an isoprenoid mentioned herein. The nucleic acid sequence can encode a biosynthetic enzyme required for isoprenoid production, e.g., isopentenyl diphosphate isomerase, geranylgeranyl diphosphate synthase, 1-deoxyxylulose 5-phosphate synthase, phosphoenolpyruvate synthase, farnesyl diphosphate synthase, geranylgeranyl diphosphate synthase, phytoene synthase, phytoene desaturase, or lycopene cyclase. One precursor of isoprenoids can be pyruvate. Pyruvate concentrations are related to acetate and acetylphosphate concentrations. Accordingly, in this instance, the second metabolite is acetyl phosphate. The promoter responding to acetyl phosphate can be controlled by a response regulator protein, e.g., a response regulator protein mentioned above. Such a promoter may only respond to acetyl phosphate in a specific host cell. In a particular example, the promoter responding to acetyl phosphate concentration is bound by *E. coli* ntrC, e.g., *E. coli* glnAp$_2$ promoter.

The promoter can be regulated by cAMP. The promoter can be a bacterial promoter which binds CAP (catabolite activator protein). In mammals, the promoter can be a promoter containing a cAMP response element (CRE), which binds to the proteins CREB, CREM, or ATF-1. In yeast cells, the promoter can be a promoter regulated by cAMP, or a promoter bound by proteins Gis1, Msn2, or Msn4. Another possible regulatory signal for the promoter can be fructose 1-phosphate, or fructose 6-phosphate. The *E. coli* FruR protein regulates such promoters.

The nucleic acid sequence can be contained on a plasmid. It can also contain a bacterial origin of replication and a selectable marker. The sequence can further contain a yeast or other eukaryotic origin of replication and appropriate selectable markers, and can be integrated into the genome.

The optimization of biosynthesis of heterologous compounds in host cells is reliant on sensing parameters of cell physiology and on utilizing these parameters to regulate the biosynthesis. One standard techniques in the art is to grow cells and for the user to exogenously add an agent, e.g., an inducer, to turn on genes required for biosynthesis of the desired product. It has been widely observed that high-level induction of a recombinant protein or pathway leads to growth retardation and reduced metabolic activity. (Kurland and Dong (1996) *Mol Microbiol* 21:1–4). The practice of exogenously supplying an inducer is empirical and does not monitor the availability of resources in the cell for biosynthesis. In contrast, natural pathways rely on feedback mechanisms to control such processes. The combination of certain promoters with specific genetically defined host cells and heterologous polypeptides in this invention unexpectedly results in a highly refined and versatile control circuit that regulates flux to heterologous polypeptide or metabolite synthesis in response to the metabolic state of the cell. Indeed, the dynamically controlled recombinant pathway provides for enhanced production, minimized growth retardation, and reduced toxic by-product formation. The regulation of gene expression in response to physiological state will also benefit other applications, such as gene therapy.

The details of one or more embodiments of the invention are set forth in the description below. Other features, objects, and advantages of the invention will be apparent from the description and from the claims.

DETAILED DESCRIPTION

The invention provides methods of engineering metabolic control, e.g., methods of utilizing promoters in specific host cells in order to optimize protein expression for either protein production or metabolite synthesis.

A central component of the invention is an expression cassette comprising a promoter and nucleic acid sequence encoding a heterologous polypeptide whose expression is desired. The expression cassette is constructed using standard methods in the art such that the coding nucleic acid sequence is operably linked, e.g., regulated by, the promoter. The promoter is chosen such that the promoter is regulated by a parameter of cell physiology or cell metabolic state. A variety of promoters can be used. In some applications the expression cassette is contained within a plasmid, such as bacterial plasmid with a bacterial origin of replication and a selectable marker. The expression cassette can be integrated into the genome of cells using standard techniques in the art.

If the expression cassette is to be used for engineering regulated production of a heterologous polypeptide during late logarithmic growth or during stationary phase, then the promoter can be chosen accordingly. For example, a promoter can be chosen that responds to small molecule signal, e.g., a second messenger, whose levels accumulate during late logarithmic growth or during stationary phase. The second messenger can be a molecule that accumulates as a precursor, an intermediate, or a waste product of a biochemical pathway. In bacteria, the small molecule signal can be a glycolysis intermediate, e.g., fructose 1-phosphate or fructose 6-phosphate or a glycolysis waste product, e.g., acetate or acetyl phosphate. In eukaryotic cells, cAMP concentrations are a well known signal of nutrient state.

The promoter in the expression cassette can be chosen based on the results of a large scale expression analysis experiment, e.g., a gene chip experiment. Genes which are induced by acetyl phosphate can be identified by hybridizing to a microarray labeled cDNA prepared from cells in grown in acetate and comparing the signal to a reference signal, e.g., to the signal of obtained with cDNA prepared from cells in early logarithmic growth. This experiment can be performed on both prokaryotic and eukaryotic cells, e.g., bacterial, yeast, plant and mammalian cells. For an example of such an experiment in a prokaryote, see Talaat et al. (2000) *Nat Biotechnol* 18:679–82 and Oh & Liao (2000) *Biotechnol Prog.* 16:278–86. Once a gene is identified which is expressed under the desired condition, its promoter can utilized in the expression cassette. Alternatively, the experiment can be performed by the exogenous addition of a desired molecule (e.g., a precursor in a metabolic pathway) or by manipulation of experimental conditions (e.g., growth to late logarithmic phase or growth while a biosynthetic enzyme is overproduced). Promoters can be identified based on the genes induced.

In one instance, an expression cassette is used for engineering regulated production of a metabolite in a bacterial cell. The promoter can be selected which is regulated by a second metabolite whose concentration is indicative of the availability of a precursor for the biosynthesis of the first metabolite. For example, if the first metabolite is an isoprenoid which is synthesized from the precursors, pyruvate and glyceraldhyde 3-phosphate, then the second metabolite can be acetyl phosphate. In a rich environment, cells produce an excess amount of acetyl-CoA, a product of pyruvate. The excess acetyl-CoA is used to produce ATP and acetate, which is secreted as a waste product. Acetate concentration increases with cell density. Acetate, acetyl-CoA, and acetyl-phosphate concentrations are interrelated by to the following biochemical reactions:

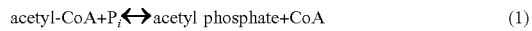
acetyl-CoA+P$_i$↔acetyl phosphate+CoA (1)

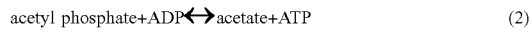
acetyl phosphate+ADP↔acetate+ATP (2)

Thus, high acetyl phosphate concentration is indicative of excess acetyl-CoA and excess pyruvate. A host cell which is genetically modified by deletion or mutation of glnL, for example, causes ntrC function to become acetyl phosphate dependent (Feng et al. (1992) *J Bacteriol* 174:6061–6070). In this fashion, a promoter regulated by ntrC, e.g., the glnAp2 promoter, can be used to control gene expression in response to acetyl phosphate. The glnAp2 promoter can be obtained using standard techniques in the art. For example, primers can be designed and synthesized that anneal to the glnAp2 promoter. The polymerase chain reaction (PCR) can be used to amplify a nucleic acid fragment containing the glnAp2 promoter. This fragment can now be used for further constructions. Likewise, an *E. coli* strain containing deletion of histidine protein kinase gene, e.g., glnL can be easily prepared. See Link et al. (1997) *J. Bacteriol.* 179(20): 6228–6237 for a detailed description of one possible method. The sequences encoding a desired heterologous polypeptide can be cloned downstream of the glnAp2 promoter so that it is operably linked to the promoter. A host cell with an inactivated glnL gene can then be transformed with the sequences. The transformed strain can be grown, and polypeptide production monitored during the course of growth. Robust protein expression can be observed at high cell densities, as in Farmer and Liao (2000) *Nat. Biotechnol* 18:533–537, the contents of which are hereby incorporated by reference.

A mammalian cell can be used as a host cell for polypeptide or metabolite production. A promoter can be selected, e.g., a promoter that responds to cAMP. Such a promoter can contain a cAMP response element (CRE), which binds to the proteins CREB, CREM, or ATF-1. Using standard techniques in the art, a desired coding sequence can be placed under control of the promoter and transformed into the mammalian cell. In some instances, the construction can be inserted into a virus, e.g., an inactivated virus. Such implementations allow for the regulated production of a protein or a metabolite produced by a heterologous biosynthetic enzyme in a gene therapy scenario. Plant cells can also be used as host cells. Again, an appropriate promoter can be chosen, e.g., a promoter than responds to a plant hormone, metabolite, or a precursor for the production of a desired metabolite. A promoter can be identified by a microarray experiment. After fusion of a desired promoter to a desired coding sequence in an appropriate vector, the construction can be electroporated into *Agrobacterium tumefaciens* and then used to transform plant cells using standard methods in the art. In still another example, yeast cells can be manipulated to express heterologous polypeptides or metabolites under metabolic control. For example, a *Saccharomyces cerevisiae* promoter can be a promoter regulated by cAMP, e.g., a promoter bound by proteins Gis1, Msn2, or Msn4. The regulation of all yeast genes in response to a variety of metabolic conditions is increasingly well studied. For example, DeRisi et al. (1997) *Science* 278:680–686 describe experiments following the transcriptional profile of nearly the entire *Saccharomyces cerevisiae* gene set under various metabolic conditions. Promoters regulated by a desired metabolite can be selected based on such data. The generation of yeast plasmids and the transformation of yeast are well known in the art.

A variety of metabolic pathways can be reconstructed using the expression techniques described above. For example, a pathway to produce lycopene can be introduced in *E. coli* by constructing expression vectors for the following genes: dxs (coding for 1-deoxy-D-xylulose 5-phosphate synthase) from *E. coli*, gps (coding for geranylgeranyl diphosphate (GGPP) synthase) from *Archaeoglobus fulgidus*, and crtBI (coding for phytoene synthase and desaturase, respectively) from *Erwinia uredovora*. These genes can reside on a single or multiple plasmids, or can be integrated into the *E. coli* chromosome. In addition, phosphoenolpyruvate synthase can be overexpressed using any method, e.g., by fusion to the glnAp2 promoter. Isopentyl diphosphate isomerase can be overexpressed using any method, e.g., by fusion to the glnAp2 promoter.

In another example, a pathway to produce polyhydroxyalkanoates (PHA), e.g., polyhydroxybutyrate can be implemented in *E. coli*. PHA is a family of linear polyesters of hydroxy acids with a variety of thermoplastic properties and commercial uses. *Pseudomonas aeruginosa* genes encoding 3-ketoacyl coenzyme A reductases and poly-3-hydroxyalkanoate polymerase can be placed under regulation of a desired promoter, e.g., glnAp2, since acetyl-CoA levels can be indicative of precursor availability for PHA synthesis.

Without further elaboration, it is believed that the above description has adequately enabled the present invention. The following examples are, therefore to be construed as merely illustrative, and not limitative of the remainder of the disclosure in any way whatsoever. All publications cited herein are hereby incorporated by reference in their entirety.

Methods

Growth conditions. All *E. coli* strains were grown in shake flasks containing the designated medium at 37° C. in waterbath shakers (Model G76; New Brunswick Scientific, Edison, N.J.). The cultures were grown in minimal media consisting of either M9 defined salts 34 containing 0.5% (wt/vol) glucose or YE defined salts containing 1.5% (wt/vol) glucose. YE defined salts consisted of (per liter) 14 g $K_2HPO_4$, 16 g $KH_2PO_4$, 5 g $(NH_4)_2SO_4$, 1 g $MgSO_4$, and 1 mg thiamine. Cell turbidity was monitored spectrophotometrically at 550 nm. Metabolite measurements. Acetate, pyruvate, and other organic acids were measured using HPLC (Constametric 3500 Solvent Delivery System and Spectromonitor 3100 Variable Wavelength Detector; LDC Analytical, Riviera Beach, Fla.) over an organic acids column (Aminex HPX-87H, Bio-Rad Laboratories, Hercules, Calif.) maintained at 65° C. The mobile phase consisted of 0.01 N H2SO4 and its flow rate was kept at 0.6 ml $min^{-1}$. Peaks coming off the column were detected at 210 nm. Glucose was measured using Sigma kit no. 315–100. To quantify lycopene, 1 ml of bacterial culture was extracted with acetone, centrifuged, and the supernatant absorbance was measured at 474 nm. Lycopene concentrations were calculated by comparing absorbances to a standard curve.

SDS-PAGE and enzyme assays. The protocol for SDS-PAGE is as described by Laemmli (1970) *Nature* 227: 680–685. Measurement of β-galactosidase activity was carried out essentially as described by Miller (1992) *A Short Course in Bacterial Genetics*, Cold Spring Harbor Laboratory Press, Cold Spring Harbor N.Y.

Results

Usage of the glnAP2 promoter in *E. coli* in a heterologous fusion to lacZ.

Increasing levels of acetyl phosphate can be an indicator of excess glucose flux. The current invention features host cells, nucleic acids sequences, and methods of utilizing acetyl phosphate as a signal to regulate the expression of rate-controlling enzymes in a desired metabolic pathway, both to utilize fully the excess carbon flux and to redirect the flux away from the toxic product, acetate.

In order to examine the potential of glnAp2 as a dynamic controller of product expression, a nucleic acid sequence was constructed containing a heterologous lacZ gene operably linked to the glnAp2 promoter. The glnAp2 promoter region containing the promoter and two ntrC-binding sites can be easily obtained by standard methods known in the art. The glnAp2 promoter was PCR-amplified from *E. coli* genomic DNA using the forward primer 5'-CAGCTG-CAAAGGTCATTGCACCAAC (containing an engineered PvuII site) and the reverse primer 5'-GGTACCAGTACGT-GTTCAGCGGACATAC (containing an engineered KpnI site). These two primers amplified a region between positions 93 and 343 in the published DNA sequence 16 (GenBank accession No. M10421).

The glnAp2 PCR fragment was also cloned into the EcoRI site of pRS551, thus generating p2GFPuv, which contains glnAp2 in front of a promoterless lacZ gene. The glnAp2-lacZ region was transferred to λRS45 via homologous recombination (Simons et al.(1987) *Gene* 53:85–96), generating phage λp2GFPuv. JCL1595 and JCL1596 were constructed by integrating a glnAp2-lacZ fusion via infection (Silhavy et al. (1984) *Experiments with Gene Fusions*, Cold Spring Harbor Laboratory Press, Cold Spring Harbor N.Y.) with λp2GFPuv phage into the chromosomes of BW13711 (lacX74) and BW18302 (lacX glnL2001, Feng et al. supra), respectively. This strain contains the glnL2001 allele, which consists of an internal deletion between codons 23 and 182 of the glnL coding sequence and presumably results in a null mutation (Feng et al. supra).

The time course of the β-galactosidase (β-gal) activity was measured in wild-type and in the glnL mutant. The glnAp2-β-gal activity increases in a time-dependent fashion similar to the excreted acetate concentration from the glnL host (JCL1596), whereas no induction of promoter activity was found for the isogenic wild-type control (JCL 1595).

TABLE 1

β-galactosidase activity of glnAp2-lacZ

|  | β-galactosidase activity (nmol/min-mg protein) | |
| --- | --- | --- |
|  | 6 hours | 11 hours |
| glnAp2-lacZ in WT (JCL1595) | <100 | ~100 |
| glnAp2-lacZ in glnL (JCL1596) | ~700 | ~1500 |
| $P_{lac}$-lacZ in (VJS632) | ~500 | ~550 |

Thus, in the absence of glnL, glnAp2 is capable of responding to the excess carbon flux that is indicated by acetate excretion. As the cells approached the late-exponential phase, the biosynthetic requirement decreased and the cells began to exhibit an excess carbon flux, as demonstrated by the increased generation of acetate. At this point, at approximately 6 hours, unexpectedly glnAp2-β-gal activity began to rise to (~700 nmol/min-mg protein, see Table 1) whereas glnAp2-β-gal activity in the wild-type strain (JCL 1595) was relatively low and remained constant throughout (~100 nmol/min-mg protein, Table 1). After more than 10 hours, glnAp2-β-gal activity in the absence of glnL was a remarkable ~1500 nmol/min-mg protein (Table 1). The induction profile of glnAp2 is also in stark contrast to that of the lac promoter ($P_{lac}$). Chromosomal $P_{lac}$ activity in strain VJS632 (lac⁺) rapidly increased after induction with IPTG (isopropyl-β-D-thio-galactopyranoside) and achieved a constant level of expression in the cell (~550 nmol/min-mg protein, see Table 1), which is independent of the growth phase.

Usage of the glnAP2 promoter in E. coli in a Heterologous Fusion to pps and aroG Expression of two different metabolic enzymes, phosphoenolpyruvate synthase (pps) and 3-deoxy-D-arabinoheptulosonate 7-phosphate (DAHP) synthase (aroG) were placed under the control of the glnAp2 promoter. As controls, these same two proteins also were overexpressed from the tac promoter ($P_{tac}$), which exhibits static control, under the same genetic background and environmental conditions. Standard methods of expressing pps leads to growth retardation (Patnaik et al. (1992) *J Bacteriol* 174:7527–7532).

Plasmid pAROG was constructed by cloning a PCR fragment containing aroG pRW5tkt into the EcoRI-BanHI sites of pJF118EH. Plasmid pPS706 has been previously described in Patnaik et al. supra. Both plasmid express the respective genes under the $P_{tac}$ promoter. The PCR fragment containing the glnAp2 promoter was cloned into the EcoRV-EcoRI sites of plasmids pAROG, and pPS706 to generate plasmids p2AROG3, and pPSG706, respectively containing the respective genes under the glnAp2 promoter.

Host strain BW18302 (lacXglnL2001) was transformed with all four plasmids. The strains with the respective plasmids were grown in M9 salts-glucose media. Growth was compared after 5 hours.

TABLE 2

Growth of Overexpressing Strains

| | $OD_{550}$ after 5 hours growth |
|---|---|
| No plasmid | ~0.5 |
| $P_{tac}$-aroG | ~0.5 |
| glnAp2-aroG | ~0.5 |
| $P_{tac}$-pps | ~0.12 |
| glnAp2-pps | ~0.4 |

As previously demonstrated, overexpression of pps using $P_{tac}$-pps caused marked growth retardation. However, the use of glnAp2 unexpectedly resulted in close to normal growth (Table 2). After 15 hours, proteins were isolated from each strain and analyzed on a 10% SDS-PAGE gel. At least 500% more pps protein was expressed when the pps gene was controlled by the glnAp2 promoter compared to the $P_{tac}$ promoter. In another surprising finding, AroG protein, whose conventional overexpression is not overtly detrimental, was also at least 300% more abundant in extracts from cells utilizing glnAp2 promoter for expression compared to the $P_{tac}$ promoter.

Production of Lycopene in E. coli by idi Overexpression

We reconstructed a recombinant lycopene pathway in *E. coli* by expressing the genes dxs (coding for 1-deoxy-D-xylulose 5-phosphate synthase) from *E. coli*, gps (coding for geranylgeranyl diphosphate (GGPP) synthase) from *Archaeoglobus fulgidus*, and crtBI (coding for phytoene synthase and desaturase, respectively) from *Erwinia uredovora*. These genes were inserted into pCL1920, a low-copy-number plasmid, to form pCW9, and simultaneously overexpressed.

We used the glnAp2 promoter to control the expression of idi (isopentenyl diphosphate isomerase). Constructs containing the idi gene were derived from a promoterless vector, pJF118, The glnAp2 promoter was inserted to form p21DI. As a control, the $P_{tac}$ promoter was inserted to form pTacIDI. These plasmids were separately introduced into a glnL strain (BW18302) containing pCW9. The p21DI-containing strain (glnAp2-idi) produced 100 mg $L^{-1}$ lycopene after 26 h in a defined medium containing glucose. The strain containing $P_{tac}$-idi on the other hand, produced only a small amount of lycopene, (<5 mg $L^{-1}$) under identical conditions. Additionally, the p21DI strain produced almost threefold less acetate than pTacIDI, which indicates that the carbon flux to acetate was being rechanneled to lycopene.

TABLE 3

Carbon yield of lycopene formation in batch cultures of E. coli.

| | Lycopene Carbon yield on glucose (mol C/mol C) |
|---|---|
| Host only (BW18302) | 0.0000 |
| +pTacIDI (Ptac-idi) | 0.0003 |
| +pTacIDI (Ptac-idi)/pPS184 (Ptac-pps) | 0.0012 |
| +p2IDI (glnAp2-idi) | 0.014 |
| +p2IDI (glnAp2-idi)/pPSG184 (glnAp2-pps) | 0.022 |

Use of pps to Enhance Lycopene Yield pps was overexpressed from gnlAp2 from another compatible plasmid, pPSG18 while the remainder of the lycopene pathway (dxs, gps, crtBI) was expressed using pCL1920. Coexpression of pps and idi with the lycopene pathway increased the final titer of lycopene by 50% and caused the productivity to increase by threefold, from 0.05 mg $mL^{-1}h^{-1}$ to 0.16 mg $mL^{-1}$ $h^{-1}$ (Table 3) This is in contrast to the companion strain containing both pTacIDI and pPS 184 ($P_{tac}$-idi+$P_{tac}$-pps), where no significant improvement in yield was observed and substantial growth inhibition occurred.

Additional Host Cells for Lycopene Production

The pykF::cat and pyk::kan alleles were introduced into a wild-type strain, in order to generate two single mutants (JCL1610 (pykF) and JCL1612 (pyk4)) and one double mutant strain (JCL 1613 (pyk FpykA)) (Ponce et al. (1995) *J Bacteriol* 177:5719–5722). The double mutant strain was able to achieve a final lycopene titer of about 14 mg lycopene/g dried cells, while the single mutant strains each obtained lycopene titers of about 2.5 mg lycopene/g dried cells. The single pyk mutants produced lycopene at a level similar to the wild type strain, ~4 mg lycopene/g dried cells. Further, overexpression of Pck, phosphoenolpyruvate carboxykinase, increased the final lycopene titer by about 3-fold. Overexpression of Ppc, phosphoenolpyruvate carboxylase, reduced lycopene production by about 30%.

OTHER EMBODIMENTS

A number of embodiments of the invention have been described. Nevertheless, it will be understood that various modifications may be made without departing from the spirit and the scope of the present invention. Accordingly, other embodiments are within the scope of the following claims. For example, all homologs of the mentioned polypeptides and genes are within the scope of this invention.

What is claimed is:

1. An *E. coli* host cell comprising a first expression cassette comprising a promoter and a nucleic acid sequence encoding isopentenyl diphosphate isomerase, geranylgeranyl diphosphate synthase, 1-deoxyxylulose 5-phosphate synthase, a phytoene synthase, or a phytoene desaturase the nucleic acid sequence being operably linked to the promoter which is bound by ntrC such that the promoter is regulated by acetyl phosphate in the absence of nitrogen starvation, wherein the cell is lacking a functional glnL histidine protein kinase gene.

2. The host cell of claim 1 wherein the host cell further comprises a nucleic acid sequence encoding a phosphoenolpyruvate synthase.

3. The host cell of claim 1 wherein the enzyme is isopentenyl diphosphate isomerase.

4. The host cell of claim 1 wherein the enzyme is geranylgeranyl diphosphate synthase.

5. The host cell of claim 1 wherein the enzyme is 1-deoxyxylulose 5-phosphate synthase.

6. The host cell of claim 1 wherein the promoter is glnAp2.

7. A kit comprising (i) a nucleic acid sequence containing a promoter bound by ntrC such that the promoter is regulated by acetyl phosphate in a defined bacterial host cell, and a coding sequence that encodes; isopentenyl diphosphate isomerase, geranylgeranyl diphosphate synthase, 1-deoxyxylulose 5-phosphate synthase, a phytoene synthase, a phytoene desaturase, or a lycopene cyclase and (ii) the defined host cell which is an *E. coli* host cell genetically modified by deletion or inactivating mutation of the glnL gene.

8. The kit of claim 7 wherein the promoter is the glnAp2 promoter.

9. A method of producing a lycopene in a bacterial host cell, the method comprising:

providing the host cell of claim 1; and expressing a 1-deoxy-D-xylulose 5-phosphate synthase, a geranylgeranyl diphosphate synthase, a phytoene synthase, and a phytoene desaturase in said host cell, at least one of which is expressed from the first expression cassette.

10. The method of claim 9 further comprising culturing the host cell under nitrogen rich conditions.

11. The method of claim 10 in which the culturing comprises growth to late logarithmic growth.

12. The method of claim 9 in which at least 5 mg $L^{-1}$ of lycopene are produced.

13. The method of claim 10 in which the promoter is glnAp2.

14. The method of claim 11 in which the promoter is glnAp2.

* * * * *